(12) United States Patent
Lopes

(10) Patent No.: US 8,496,972 B2
(45) Date of Patent: Jul. 30, 2013

(54) CLEANING, DISINFECTING AND MICROBICIDAL COMPOSITIONS

(76) Inventor: John Alex Lopes, Troy, MI (US)

( * ) Notice: Subject to any disclaimer, the term of this patent is extended or adjusted under 35 U.S.C. 154(b) by 63 days.

(21) Appl. No.: 12/912,171

(22) Filed: Oct. 26, 2010

(65) Prior Publication Data

US 2011/0097422 A1    Apr. 28, 2011

Related U.S. Application Data

(60) Provisional application No. 61/279,726, filed on Oct. 26, 2009.

(51) Int. Cl.
*A01N 59/02* (2006.01)
*A61K 33/04* (2006.01)

(52) U.S. Cl.
USPC .......................................... 424/703

(58) Field of Classification Search
None
See application file for complete search history.

(56) References Cited

U.S. PATENT DOCUMENTS

| 4,375,421 | A | * | 3/1983 | Rubin et al. | 510/403 |
| 5,000,944 | A | * | 3/1991 | Prencipe et al. | 424/57 |
| 5,104,644 | A | * | 4/1992 | Douglas | 424/53 |
| 6,120,698 | A | * | 9/2000 | Rounds et al. | 252/181 |
| 2004/0253352 | A1 | * | 12/2004 | Koefod et al. | 426/335 |
| 2006/0100119 | A1 | * | 5/2006 | Smith | 510/235 |
| 2006/0134021 | A1 | * | 6/2006 | Mackles et al. | 424/53 |
| 2006/0157415 | A1 | * | 7/2006 | Koefod | 210/670 |
| 2010/0003341 | A1 | * | 1/2010 | Besendorfer | 424/616 |
| 2010/0233289 | A1 | * | 9/2010 | Smithyman et al. | 424/637 |

FOREIGN PATENT DOCUMENTS

WO    WO 2007/014575    *    2/2007

* cited by examiner

*Primary Examiner* — James H. Alstrum-Acevedo
*Assistant Examiner* — Jessica Kassa
(74) *Attorney, Agent, or Firm* — Reising Ethington P.C.

(57) ABSTRACT

A microbicidal disinfecting composition and a method of preparing the same include the use of an acidifying agent that comprises at least one of an alkali metal bisulfate, ammonium bisulfate, or a combination thereof. The composition has broad-spectrum microbicidal properties and does not demonstrate cloudiness or precipitation when prepared, diluted, or otherwise exposed to hard water.

6 Claims, No Drawings

CLEANING, DISINFECTING AND MICROBICIDAL COMPOSITIONS

CROSS-REFERENCE TO RELATED APPLICATION

This application claims the benefit of U.S. Provisional Application No. 61/279,726 filed Oct. 26, 2009. The disclosure of the above application is incorporated herein by reference.

TECHNICAL FIELD

The technical field of this disclosure generally relates to microbicidal disinfecting compositions and methods of their preparation.

BACKGROUND

Microbicidal disinfecting compositions that include one or more microorganism-destroying antimicrobial agents as an active ingredient are used in a robust array of industrial, personal, and agricultural settings. The lethal effect of many antimicrobial agents towards microorganisms is generally enhanced at acidic pH levels. For this reason, the pH of common antimicrobial agents is typically adjusted downward by an acidifying agent in the preparation of a microbicidal disinfecting composition. Anionic surfactants such as esters of alkyl and aryl sulfates and sulfonates, for example, are often combined with mineral acids and/or organic acids to achieve a level of acidity conducive to acceptable microbicidal activity. Mineral acids such a phosphoric acid, sulfuric acid, and hydrochloric acid, for example, are often used to adjust the pH of alkyl and aryl sulfonated esters to form liquid microbicidal disinfecting compositions. Organic acids such as citric acid and lactic acid, for example, are often used to adjust the pH of alkyl and aryl sulfated or sulfonated esters and to form powder or liquid microbicidal disinfecting compositions.

A microbicidal disinfecting composition prepared with mineral and/or organic acids as the acidifying agent, however, has a tendency become cloudy and show precipitate formation in hard water. This problem is often combated by the addition of chemicals to prevent cloudiness and precipitate formation—likely by decreasing the critical micelle concentration. But the inclusion of additional chemicals into the microbicidal disinfecting composition limits the extent to which the antimicrobial agent may be concentrated. The reliance on organic acid acidifying agents may further impact this physical constraint. These acids are typically weak acids and, as such, require larger quantities to achieve the desired acidic pH level when compared to mineral acids.

The use of organic acids and/or mineral acids as the primary acidifying agent in the preparation of a microbicidal disinfecting composition can complicate handling, storage, and transportation concerns. The limits imposed on the extent of antimicrobial agent concentration by these acidifying agents and, as needed, additional chemicals to alleviate turbidity, can impact storage and transportation efficiencies. Certain mineral acids are also corrosive and may require special handling and disposal procedures.

SUMMARY

An acidifying agent that includes at least one of an alkali metal bisulfate or ammonium bisulfate, both of which exhibit high aqueous solubility, may be used to form a microbicidal disinfecting composition. These bisulfates help form an economical, generally non-hazardous, and stable microbicidal disinfecting composition for use in the food processing, healthcare, personal care, and agricultural industries, to name but a few. The microbicidal disinfecting composition may be prepared in the form of a powder, a liquid solution, a gel, a foam, a fog, a mist or as on a wipe.

A low concentration of the acidifying agent can provide the desired acidity for a wide variety of antimicrobial agents without inducing cloudiness or precipitation when exposed to hard water. This dual-functionality of the acidifying agent may provide a number of economic and product-application advantages. The use of an alkali metal bisulfate and/or ammonium bisulfate as all or part of the acidifying agent, for example, allows for more concentrated microbicidal disinfecting compositions to be prepared. The presence of additional chemicals to inhibit cloudiness and precipitation may not be needed due to the hard water tolerance of the alkali metal bisulfate and ammonium bisulfate. The ability to achieve high antimicrobial agent concentrations can reduce storage and transportation costs. As another example, the hazards associated with handling, storing, and transporting microbicidal disinfecting compositions—both concentrated and ready-for-use—made with corrosive mineral acids can be avoided. Alkali metal bisulfates and ammonium bisulfate also cost less than organic acid and some mineral acid acidifying agents. This cost difference in conjunction with the low concentration effectiveness of the acidifying agent may translate into raw material and/or production savings.

The acidifying agent may, in one embodiment, comprise at least one of sodium bisulfate, potassium bisulfate, ammonium bisulfate, or combinations thereof. Each of these bisulfates is available in food grade and technical grade. A food grade quality may be used when the microbicidal disinfecting composition is meant to disinfect food contact surfaces, or be included in an animal or public health product. A technical grade quality may be used for other appropriate purposes. The acidifying agent may be employed with a number of antimicrobial agents including anionic, cationic, and nonionic surfactants. A small sampling of exemplary antimicrobial agents include sodium dodecyl sulfate, sodium dioctyl sulfosuccinate, sodium decyl lactylate, sodium dodecyl benzene sulfonate, and a quaternary ammonium compound. Other agents may also be present in the microbicidal disinfecting composition including a fungicidal agent, a preservative, a flavoring agent, a coloring agent, a freeze-thaw modifying agent, or a sequestering agent. The addition of a fungicidal agent, such as a copper or zinc salt, can afford the microbicidal disinfecting composition with antifungal and algicidal characteristics.

Other exemplary and more detailed embodiments of the invention will become apparent from the detailed description that follows.

DETAILED DESCRIPTION

A microbicidal disinfecting composition may include an antimicrobial agent and an acidifying agent. The acidifying agent may include at least one of an alkali metal bisulfate or ammonium bisulfate and may be present in an amount effective to provide the microbicidal disinfecting composition with an acidity conducive to the desired microbicidal activity of the antimicrobial agent. The pH value of the microbicidal disinfecting composition may range from very low up to 7.0 depending on the current state of the composition or its intended use (highly concentrated for shipping/storage, less concentrated for end-use application, etc.). The amount of the acidifying agent needed to achieve this pH value target can vary quit considerably and may range from about 0.1 wt. % to about 99.90 wt. %. The microbicidal disinfecting composition may also include, if desired, at least one of a fungicidal agent, a preservative, a flavoring agent, a coloring agent, a freeze-thaw modifying agent, or a sequestering agent.

The alkali metal bisulfate and/or ammonium bisulfate may, at low concentrations, provide the microbicidal disinfecting composition with the acidity needed to support the effectiveness of the antimicrobial agent. The presence of hard water in the microbicidal disinfecting composition or the later addition of hard water will not promote turbidity or precipitate formation. The use of an alkali metal bisulfate and/or ammonium bisulfate generally contributes to the formation of a clear solution when the microbicidal disinfecting composition is in a liquid aqueous state. The low concentration effacacy of these bisulfates and their hard water tolerance can simplify, and reduce the costs associated with, the preparation of the microbicidal disinfecting composition as compared to other similar compositions that use mineral acids and/or organic acids as the primary acidifying agent.

A method of preparing the microbicidal disinfecting composition may include adding the acidifying agent to a liquid medium that includes an antimicrobial agent. The acidifying agent may be added in an amount effective to considerably lower the pH value of the liquid medium to form an acidic concentrate. The acidic concentrate of the microbicidal disinfecting composition may then be shipped or stored, either in liquid or powder form. The fact that additional chemicals do not have to be included in the acidic concentrate to prevent turbidity or precipitation when the microbicidal disinfecting composition is exposed to hard water increases the extent to which the antimicrobial agent may be concentrated. Then, at some later time, the acidic concentrate may be diluted with water to form some intermediate microbial disinfecting composition or an end-use microbicidal disinfecting composition.

The alkali metal bisulfate may be sodium bisulfate, potassium bisulfate, or a combination of sodium bisulfate and potassium bisulfate. Each of these alkali metal bisulfates as well as ammonium bisulfate is available in food grade and technical grade. The selection of which grade to select for use in preparing the microbicidal disinfecting composition depends on the particular use for which the composition is intended, as understood by skilled artisans. The antimicrobial agent may be an anionic surfactant, a cationic surfactant, a nonionic surfactant, or any other material that exhibits microbicidal activity in acidic conditions. The antimicrobial agent may be present in an amount ranging from about 0.0001 wt. % to about 50 wt. %.

An anionic surfactant that may be employed as the antimicrobial agent may comprise a C4-C18 acid or salt compound selected from the group consisting of: (1) an alkyl-carboxylate, isethionate, sulfate, sulfonate, sulfoacetate, sulfosuccinate, lactate, lactylate, phosphate, phosphonate, or mixtures thereof; (2) an alkenyl-carboxylate, isethionate, sulfate, sulfonate, sulfoacetate, sulfosuccinate, lactate, lactylate, phosphate, phosphonate, or mixtures thereof; (3) an alkylbenzenecarboxylate, isethionate, sulfate, sulfonate, sulfoacetate, sulfosuccinate, lactate, lactylate, phosphate, phosphonate, or mixtures thereof; or (4) a naphthalene-carboxylate, isethionate, sulfate, sulfonate, sulfoacetate, sulfosuccinate, lactate, lactylate, phosphate, phosphonate, or mixtures thereof.

A more specific class of anionic surfactants that may be used include a free acid or a salt of (1) a C6-C18 alkyl sulfate, (2) a C6-C18 alkenyl sulfate, (3) a C6-C18 alkyl ether sulfate, (4) a C6-C18 alkenyl ether sulfate, (5) a C8-C16 alkyl diphenyl ether disulfonate, (6) a C4-C18 fatty acid isethionate, (7) a C6-C18 alkyl sulfonate, (8) a C6-C18 alkenyl sulfonate, (9) a dialkyl sulfosuccinate in which the alkyl group independently contains from 6 to 18 carbon atoms, (10) a dialkenyl sulfosuccinate in which the alkenyl group independently contains from 6 to 18 carbon atoms, (11) a C6-C18 alkylbenzene sulfonate, (12) a naphthalene sulfonate, (13) an alkyl naphthalene sulfonate in which the alkyl group independently contains from 1 to 6 carbon atoms, (14) a mono (n-alkyl) acyl ester of a C2-C4 hydroxylated monocarboxylic acid in which the alkyl group independently contains from 6 to 18 carbon atoms, (15) a mono (n-alkenyl) acyl ester of a C2-C4 hydroxylated monocarboxylic acid in which the alkyl group independently contains from 6 to 18 carbon atoms, (16) a mono (n-alkyl) acyl ester of a C2-C4 hydroxylated dicarboxylic acid in which the alkyl group independently contains from 6 to 18 carbon atoms, (17) a mono (n-alkenyl) acyl ester of a C2-C4 hydroxylated dicarboxylic acid in which the alkenyl group independently contains from 6 to 18 carbon atoms, (18) a mono (n-alkyl) alkyl ester of a C2-C4 dicarboxylic acid in which the alkyl group independently contains from 6 to 18 carbon atoms, (19) a mono (n-alkenyl) alkyl ester of a C2-C4 dicarboxylic acid in which the alkenyl group independently contains from 6 to 18 carbon atoms, and (20) a C4-C18 fatty alcohol sulfoacetate.

Some preferred exemplary anionic surfactants that may be used as the antimicrobial agent include at least one of a sulfated alkyl ester, a sulfated aryl ester, a sulfonated alkyl ester, or a sulfonated aryl ester. Some specific examples of such anionic surfactants are sodium dodecyl sulfate, sodium dioctyl sulfosuccinate, sodium decyl lactylate, and sodium dodecyl benzene sulfonate.

A cationic surfactant that may be employed as the antimicrobial agent may comprise, for example, a quaternary ammonium compound. Other cationic and nonionic surfactants known to skilled artisans may also be used as the antimicrobial agent.

The fungicidal agent may be any material that exhibits fungicidal activity such as copper salts and zinc salts. Some specific fungicidal agents that may be included in the microbicidal disinfecting composition include copper sulfate, cupric sulfate, and zinc sulfate. These metal salts can provide the microbicidal disinfecting composition with antifungal and algicidal characteristics in the presence of the acidifying agent. The fungicidal agent may be present in an amount ranging up to about 10 wt. %.

The preservative, flavoring agent, coloring agent, freeze-thaw modifying agent, and sequestering agent may be any material known to skilled artisans. The preservative may, for example, be a free acid, salt, or ester form of at least one of benzoic acid, sorbic acid, ascorbic acid, or erythorbic acid. The flavoring agent may be any known agent that imparts a specific flavor (meat flavor, seafood flavor, fruity flavor, herbal flavor, etc.). These materials are generally commercially available. The coloring agent may be any coloring agent suitable for the intended use of the microbicidal disinfecting composition. The freeze-thaw agent may be any known organic or inorganic material that can be used to increase or decrease the freezing point of the microbicidal disinfecting composition. Some specific examples of freeze-thaw agents include an alcohol, an inorganic salt, and urea. The sequestering agent may be any material that binds to metal or toxic compounds. Specific examples of suitable sequestering agents include, for example, sodium acid pyrophosphate, citric acid, isopropyl citrate, and calcium diacetate. Each of the preservative, flavoring agent, coloring agent, freeze-thaw modifying agent, and sequestering agent may be included in the microbicidal disinfecting composition in an amount that independently ranges from about 0.0001 wt. % to about 10 wt. %.

EXAMPLES

The Examples in Table 1 detail the preparation of several exemplary microbicidal disinfecting compositions. An anionic surfactant was used as the antimicrobial agent and sodium bisulfate was used as the acidifying agent. The compositions were diluted with water for determining their microbicidal efficacy.

Example 1

Composition A

| Ingredients | % w/w |
|---|---|
| Sodium dodecylbenzene sulfonate | 33.33% |
| Sodium bisulfate | 66.67% |
| Total Wt | 100.00% |
| pH of 0.1% | 2.54 |

Example 2

Composition B

| Ingredients | % w/w |
|---|---|
| Sodium dodecylbenzene sulfonate | 26.67% |
| Citric acid | 20.00% |
| Benzoic acid | 13.33% |
| Sodium bisulfate | 40.00% |
| Total Wt | 100.00% |
| pH of 0.1% | 2.54 |

Example 3

Composition C

| Ingredients | % w/w |
|---|---|
| Sodium dodecylbenzene sulfonate | 13.33% |
| Sodium bisulfate | 20.00% |
| Lactic acid | 33.33% |
| Water | 33.33% |
| Total Wt | 100.00% |
| pH of 0.2% | 2.54 |

Example 4

Composition D

| Ingredients | % w/w |
|---|---|
| Copper sulfate | 10.00% |
| Sodium bisulfate | 90.00% |
| Total Wt | 100.00% |
| pH of 0.1% | 2.54 |

Example 5

Composition E

| Ingredients | % w/w |
|---|---|
| Copper sulfate | 0.98% |
| Sodium dodecylbenzene sulfonate | 2.44% |
| Sodium bisulfate | 96.59% |
| Total Wt | 100.00% |
| pH of 0.1% | 2.54 |

The microbicidal efficacy of the microbicidal disinfecting compositions of Examples 1-3 (compositions A-C) were evaluated with 50 ppm of hypochlorite as a control against *Staphylococcus aureus* and *Escherichia coli* by the modified detergent and germicidal sanitizer test of the A.O.A.C. (Lopes, 1986). The results are shown in Table 1.

TABLE 1

| Sanitizing Composition | % w/v | % Kill Staph. aureus | E. coli |
|---|---|---|---|
| Example 1 | 0.10 | >99.999 | >99.999 |
| Example 2 | 0.10 | >99.999 | >99.999 |
| Example 3 | 0.20 | >99.999 | >99.999 |
| Hypochlorite Control | 50 ppm | >99.999 | >99.999 |

The microbicidal efficacy of the microbicidal disinfecting composition of Example 1 (composition A) was further tested and proven effective against *Salmonella* on contaminated tomatoes. When *Salmonella*-contaminated tomatoes were treated with 0.1% solution of composition A, the viable bacterial population was reduced by 2.31 $\log_{10}$ CFU as compared with 2.11 $og_{10}$ CFU with 150 ppm of hypochlorite.

What is claimed is:
1. A microbicidal disinfecting composition consisting of: water; an anionic surfactant; and
an amount of an acidifying agent effective to provide the microbicidal disinfecting composition with a pH value of 7.0 or below, wherein the acidifying agent is selected from the group of an alkali metal bisulfate, ammonium bisulfate, and a combination thereof.
2. The microbicidal disinfecting composition of claim 1, wherein the alkali metal bisulfate comprises at least one of sodium bisulfate, potassium bisulfate, or a combination thereof.

3. The microbicidal disinfecting composition of claim 1, wherein the anionic surfactant is present in an amount that ranges from about 0.0001 wt. % to about 50 wt. %, the amount of the acidifying agent ranges from about 0.1 wt. % to about 99.90 wt. %, and the balance is water.

4. The microbicidal disinfecting composition of claim 1, wherein the anionic surfactant comprises at least one C4-C18 acid or salt compound selected from the group consisting of: (1) an alkyl- carboxylate, isethionate, sulfate, sulfonate, sulfoacetate, sulfosuccinate, lactate, lactylate, phosphate, phosphonate, or mixtures thereof; (2) an alkenyl- carboxylate, isethionate, sulfate, sulfonate, sulfoacetate, sulfosuccinate, lactate, lactylate, phosphate, phosphonate, or mixtures thereof; (3) an alkylbenzene- carboxylate, isethionate, sulfate, sulfonate, sulfoacetate, sulfosuccinate, lactate, lactylate, phosphate, phosphonate, or mixtures thereof; (4) a naphthalene- carboxylate, isethionate, sulfate, sulfonate, sulfoacetate, sulfosuccinate, lactate, lactylate, phosphate, phosphonate, or mixtures thereof; or (5) a combination of any of the C4-C18 organic acid or salt compounds of (1)-(4).

5. The microbicidal disinfecting composition of claim 4, wherein the anionic surfactant comprises at least one of a sulfated alkyl ester, a sulfated aryl ester, a sulfonated alkyl ester, or a sulfonated aryl ester, or combinations thereof.

6. The microbicidal disinfecting composition of claim 5, wherein the anionic surfactant comprises at least one of sodium dodecyl sulfate, sodium dioctyl sulfosuccinate, sodium decyl lactylate, sodium dodecyl benzene sulfonate, or combinations thereof.

* * * * *